United States Patent [19]

Dubief et al.

[11] Patent Number: 5,470,551
[45] Date of Patent: Nov. 28, 1995

[54] USE IN COSMETICS OR IN TOPICAL APPLICATION OF AN AQUEOUS DISPERSION BASED ON ORGANOPOLYSILOXANES AND ON A CROSS-LINKED ACRYLAMIDE/NEUTRALIZED 2-ACRYLAMIDO-2-METHYLPROPANESULFONIC ACID COPOLYMER

[75] Inventors: Claude Dubief, Le Chesnay; Daniele Cauwet, Paris, both of France

[73] Assignee: L'Oreal, Paris, France

[21] Appl. No.: 64,144

[22] PCT Filed: Sep. 15, 1992

[86] PCT No.: PCT/FR92/00866

§ 371 Date: May 17, 1993

§ 102(e) Date: May 17, 1993

[87] PCT Pub. No.: WO93/05762

PCT Pub. Date: Apr. 1, 1993

[30] Foreign Application Priority Data

Sep. 17, 1991 [FR] France ................. 9111439

[51] Int. Cl.$^6$ .............. A61K 31/78; A61K 31/785; A61K 7/075
[52] U.S. Cl. ............. 424/70.12; 424/78.03; 424/78.35; 424/59; 424/70.122

[58] Field of Search ............. 424/78.1, 70, 71, 424/70.17, 78.03, 78.35, 59, 70.122, 70.121; 526/240

[56] References Cited

U.S. PATENT DOCUMENTS

| | | | |
|---|---|---|---|
| 3,129,195 | 4/1964 | June et al. | 526/240 |
| 3,692,673 | 9/1972 | Hope | 526/240 |
| 4,652,621 | 3/1987 | Kodono et al. | 526/262 |
| 4,710,374 | 12/1987 | Grollier et al. | 424/71 |
| 4,737,541 | 4/1988 | Stavenger et al. | 526/240 |
| 4,983,383 | 1/1991 | Maksimoski et al. | 424/71 |
| 5,160,730 | 11/1992 | Dubief et al. | 424/59 |

FOREIGN PATENT DOCUMENTS

| | | | |
|---|---|---|---|
| 0216147 | 4/1987 | European Pat. Off. | 526/240 |
| 0424260 | 4/1991 | European Pat. Off. | |
| 0359349 | 4/1991 | European Pat. Off. | |
| 0466184 | 1/1992 | European Pat. Off. | |

Primary Examiner—Peter F. Kulkosky
Attorney, Agent, or Firm—Jacobson, Price, Holman & Stern

[57] ABSTRACT

The present invention relates to the use in cosmetics or in topical application of an aqueous dispersion containing, in a cosmetically acceptable aqueous medium, at least one organopolysiloxane and one crosslinked acrylamide/neutralized 2-acrylamido-2-methylpropanesulfonic acid copolymer, with the proviso that the organopolysiloxane is not a linear dimethylpolysiloxane with a viscosity of less than $10^{-1}$ m$^2$/s.

21 Claims, No Drawings

USE IN COSMETICS OR IN TOPICAL APPLICATION OF AN AQUEOUS DISPERSION BASED ON ORGANOPOLYSILOXANES AND ON A CROSS-LINKED ACRYLAMIDE/NEUTRALIZED 2-ACRYLAMIDO-2-METHYLPROPANESULFONIC ACID COPOLYMER

The invention relates to the use in cosmetics or in topical application of an aqueous dispersion based on organopolysiloxanes and on a crosslinked acrylamide/neutralized 2-acrylamido-2-methylpropanesulfonic acid copolymer.

Silicone oils are already used in cosmetics as lubricating agents in hair and skin treatment compositions. They are mainly polydimethylsiloxanes.

In order to introduce softness to the hair or the skin, or also to facilitate disentangling of hair, cationic polymers or surface-active agents have been used for a long time. Cationic compounds have the disadvantage, after repeated applications, of making the hair lank by giving it a greasy appearance or of producing a sticky effect on the skin.

The Applicant has discovered, surprisingly, that the use of an aqueous dispersion based on organopolysiloxanes and on a crosslinked acrylamide/neutralized 2-acrylamido-2-methylpropanesulphonic acid copolymer for hair treatment makes it possible to obtain shiny, silky and lively hair whose disentangling and softness properties are substantially improved.

The use of this aqueous dispersion in skin treatment also makes it possible to confer on the skin a soft feel without a sticky effect.

The aqueous dispersions used in cosmetics or in topical application, according to the present invention, spread much more easily on the skin and the hair than the compositions of the prior art based on cationic compounds.

The Applicant has also discovered that the cosmetic compositions in the form of an aqueous dispersion, according to the present invention, were remarkably stable and that their cosmetic qualities were retained even after several successive applications and more particularly in non-rinsed application on hair.

The subject of the invention thus consists of the use in cosmetic hair or skin treatment or in topical application of an aqueous dispersion containing at least one organopolysiloxane and of one crosslinked acrylamide/neutralized 2-acrylamido-2-methylpropane-sulfonic acid copolymer.

Another subject of the invention relates to cosmetic or dermatological compositions for hair or skin treatment in the form of aqueous dispersions.

Another subject of the invention relates to processes for cosmetic hair or skin treatment using these compositions, depending upon the desired application.

Other subjects of the invention will become apparent in the light of the description and the examples which follow.

The main subject of the present invention is the use, for cosmetic hair or skin treatment, or in topical application, of an aqueous dispersion, characterized in that the latter contains, in a cosmetically or physiologically acceptable aqueous medium, at least one organopolysiloxane and one crosslinked acrylamide/neutralized 2-acrylamido-2-methylpropanesulfonic acid copolymer, with the proviso that the organopolysiloxane is not chosen from linear polydimethylsiloxanes with a viscosity of less than $10^{-1}$ m$^2$/s.

The organopolysiloxanes used in the dispersions according to the present invention are organopolysiloxane oils or organic solutions containing organosiloxane gum or resin.

Among the organosiloxanes used in accordance with the present invention, there may be mentioned, in a nonlimiting way:

I. Volatile silicones

These have a boiling point between 60° C. and 260° C. Among this type of silicone, there are mentioned:

(i) cyclic silicones containing 3 to 7 silicon atoms and preferably 4 to 5. They are, for example, octamethylcyclotetrasiloxane sold under the name of Volatile Silicone 7207 by Union Carbide or Silbione 70045 V2 by Rhône-Poulenc or decamethylcyclopentasiloxane sold under the name of Volatile Silicone 7158 by Union Carbide, or Silbione 70045 V5 by Rhône-Poulenc, as well as their mixtures.

There are also mentioned cyclocopolymers of dimethylsiloxane/methylalkylsiloxane type, such as Silicone Volatile FZ 3109 sold by the Company Union Carbide, which is a dimethylsiloxane/methyloctylsiloxane cyclocopolymer;

(ii) linear volatile silicones having 2 to 9 silicon atoms and having a viscosity less than or equal to $5.10^{-6}$ m$^2$/s at 25° C. They are, for example, hexamethyldisiloxane sold under the name Silbione 70 041 V 0.65 by the Company Rhône-Poulenc. This type of product is described in the article by Todd & Byers, "Volatile silicone fluids for cosmetics", Cosmetics and Toiletries, Vol. 91, Jan 76, p. 27–32.

II. Nonvolatile silicones

They consist mainly of polyalkylsiloxanes, polyarylsiloxanes, polyalkylarylsiloxanes, silicone gums and resins and organomodified polysiloxanes, as well as their mixtures.

Among polyalkylsiloxanes, there may mainly be mentioned linear polydimethylsiloxanes with a viscosity greater than $10^{-1}$ m$^2$/s:

either, containing trimethylsilyl end groups, such as, for example and in a non-limiting way, Silbione oils of the 70047 series marketed by Rhône-Poulenc, 47 V 500.000 oil of Rhône-Poulenc or certain Viscasils of General Electric, or containing trihydroxysilyl end groups, such as oils of the 48 V series of Rhône-Poulenc.

In this polyalkylsiloxane class, there may also be mentioned polyalkylsiloxanes sold by the Company Goldschmidt under the names Abilwax 9800 and Abilwax 9801, which are poly($C_1$–$C_{20}$)alkylsiloxanes.

Among polyalkylarylsiloxanes, there may be mentioned linear and/or branched polydimethyldiphenylsiloxanes or polydimethylphenylsiloxanes, with a viscosity $10^{-5}$ to $5.10^{-2}$ m$^2$/s at 25° C., such as, for example:

Rhodorsil 763 oil of Rhône-Poulenc,

Silbione oils of the 70641 series of Rhône-Poulenc, such as Silbione 70641 V 30 and 70641 V 200 oils of Rhône-Poulenc, the product DC 556 Cosmetic Grad Fluid of Dow Corning, silicones of the PK series of Bayer, such as PK20, silicones of the PN or PH series of Bayer, such as PN 1000 and PH 1000, certain oils of the SF series of General Electric, such as SF 1250, SF 1265, SF 1154 or SF 1023.

Silicone gums, in accordance with the present invention, are-polydiorganosiloxanes with a high molecular mass of between 200,000 and 1,000,000, used alone or as a mixture in a solvent chosen from volatile silicones, polydimethylsiloxane oils (PDMS), polyphenylmethylsiloxane oils (PPMS), isoparaffins, methylene chloride, pentane, dodecane, tridecane, tetradecane or their mixtures.

There are mentioned, for example, the following compounds:

poly[ dimethylsiloxane/methylvinylsiloxane ],
poly[ dimethylsiloxane/diphenylsiloxane ],
poly[ dimethylsiloxane/phenylmethylsiloxane ],
poly[dimethylsiloxane/diphenylsiloxane/methylvinylsiloxane].

There may be mentioned, for example, in a non-limiting way, the following mixtures:

1) mixtures formed from a polydimethylsiloxane hydroxylated at the chain ends (Dimethiconol according to the CTFA nomenclature), and from a cyclic polydimethylsiloxane (Cyclomethicone according to the CTFA nomenclature), such as the product Q2 1401 sold by the Company Dow Corning;

2) mixtures formed from a polydimethylsiloxane gum with a cyclic silicone, such as the product SF 1214 Silicone Fluid of General Electric, which is an SE 30 gum with an MW of 500,000 solubilized in SF 1202 Silicone Fluid (decamethylcyclopentasiloxane);

3) mixtures of two PDMSs having different viscosities, especially of a PDMS gum and of a PDMS oil, such as the products SF 1236 and CF 1241 of the Company General Electric. The product SF 1236 is the mixture of an SE 30 gum defined above having a viscosity of 20 $m^2/s$ and of an oil SF 96 having a viscosity of $5.10^{-6}$ $m^2/s$ (15% of SE 30 gum and 85% of SF 96 oil).

The product CF 1241 is the mixture of an SE 30 gum (33%) and of a PDMS (67%) having a viscosity $10^{-3}$ $m^2/s$.

Organopolysiloxane resins which can be used in accordance with the invention are crosslinked siloxane systems containing the units: $R_2SiO_{2/2}$, $RSiO_{3/2}$ and $SiO_{4/2}$ in which R represents a hydrocarbon group having 1 to 6 carbon atoms or a phenyl group. Among these products, those particularly preferred are those in which R denotes a lower alkyl radical or a phenyl radical.

Among these resins, there may be mentioned the product sold under the name Dow Corning 593 or those sold under the names Silicone Fluid SS 4230 and SS 4267 by the Company General Electric and which are "dimethyl/trimethylpolysiloxane".

Organomodified silicones, in accordance with the present invention, are silicones as defined above containing in their general structure one or a number of organofunctional groups attached directly to the siloxane chain or attached via a hydrocarbon radical.

There are mentioned, for example, silicones containing:

a) polyoxyethylene and/or polyoxypropylene groups, optionally containing alkyl groups, such as:
the product named dimethicone copolyol sold by the Company Dow Corning under the names DC 1248 and (C12)alkylmethicone copolyol sold by the Company Dow Corning under the name Q2 5200,
Silwet L 722, L 7500, L 77 or L 711 oils of the Company Union Carbide,
the mixture of dimethicone copolyol and of cyclomethicone such as the product sold under the name Q2-3225C by the Company Dow Corning.

b) perfluorinated groups such as trifluoroalkyls such as, for example, those sold by the Company General Electric under the names "FF.150 Fluorosilicone Fluid"

or by the Company Shin Etsu under the names X-22-819, X-22-820, X-22-821 or X-22-822;

c) hydroxyacylamino groups such as those described in European Patent Application EPA 0,342,834 and in particular the silicone sold by the Company Dow Corning under the name Q2-8413;

d) thiol groups such as the silicones X 2-8360 of Dow Corning or GP 72A and GP 71 of Genesee;

e) substituted or unsubstituted amino groups, as in GP4 Silicone Fluid of Genesee, GP 7100 of Genesee, Q2 8220 of Dow Corning, AFL 40 of Union Carbide or the silicone called "Amodimethicone" in the CTFA dictionary;

f) carboxylate groups, such as the products described in European Patent EP 186,507 of Chisso Corporation;

g) hydroxylated groups, such as polyorganosiloxanes containing hydroxyalkyl functional groups, described in French Patent Application No. FR-85 16334, corresponding to the following formula:

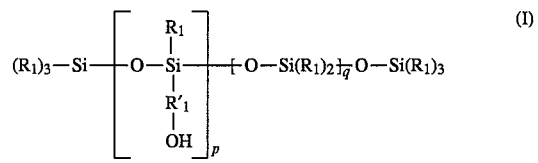

in which
the radicals $R_1$, which are identical or different, are chosen from methyl and phenyl radicals, at least 60 mol % of the radicals $R_1$ being methyl;
the radical $R'_1$ is a divalent $C_2$–$C_{18}$ alkylene hydrocarbon chain;
p is between 1 and 30 inclusive;
q is between 1 and 150 inclusive;

h) alkoxylated groups as in the silicone copolymer F 755 of SWS Silicones and the products Abilwax 2428, Abilwax 2434 or Abilwax 2440 of the Company Goldschmidt;

i) acyloxyalkyl groups, such as, for example, the polyorganopolysiloxanes described in French Patent Application No. 88 17433, corresponding to the following formula:

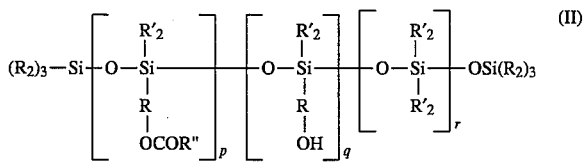

in which:
$R_2$ denotes methyl, phenyl, OCR" or hydroxyl, a single one of the $R_2$ groups per silicon atom can be OH;
$R'_2$ denotes methyl or phenyl, at least 60 mol % of the combined radicals $R_2$ and $R'_2$ is [sic] methyl;
R" denotes $C_8$–$C_{20}$ alkyl or alkenyl;
R denotes a linear or branched, divalent $C_2$–$C_{18}$ alkylene hydrocarbon;
r is between 1 and 120 inclusive;
p is between 1 and 30;
q has the value 0 or is less than 0.5 p, p+q being between 1 and 30; the polyorganosiloxanes of formula (II) can contain groups

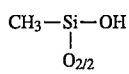

in proportions not exceeding 15% of the sum p+q+r;

j) quaternary ammonium groups, as in the products X2 81 08 and X2 81 09 or the product Abil K 3270 of the Company Goldschmidt;

k) amphoteric or betaine groups, such as in the product sold by the Company Goldschmidt under the name Abil B 9950;

l) bisulfite groups, such as in the products sold by the Company Goldschmidt under the names Abil S 201 and Abil S 255.

Particularly preferred polyorganosiloxanes, according to the present invention, are chosen from:

1) nonvolatile silicones of linear polyalkylsiloxane type containing trimethylsilyl end groups, such as Silbione oils of the 70047 and 47 series such as 47 V 500.000 oil marketed by Rhône-Poulenc, or of polyalkylarylsiloxane type such as Silbione 70641V 200 oil of Rhône-Poulenc;

2) mixtures of organosiloxanes and of cyclic silicones such as Q2 1401 of the Company Dow Corning or SF 1214 Silicone Fluid of the Company General Electric;

3) fluorosilicones of polyalkylsiloxane type containing trimethylsilyl end groups and substituted on the chain by trifluoropropyl groups such as the fluorosilicone sold by the Company Shin Et Su [sic] under the name X-22-821.

The polyorganosiloxanes used in accordance with the present invention are present in the aqueous dispersion in a proportion of between 0.5 and 50% by weight and preferably between 1 and 30% by weight with respect to the total weight of the dispersion.

The crosslinked acrylamide/2-acrylamido-2-methyl-pro-panesulfonic acid copolymer used in accordance with the present invention is more particularly a copolymer crosslinked with a compound containing olefinic poly-unsaturation such as tetraallyloxyethane, allylsucrose, allylpentaerythritol or methylenebisacrylamide, partially or completely neutralized by a neutralization agent such as sodiumhydroxide, potassium hydroxide, aqueous ammonia or an amine such as triethanolamine or monoethanolamine.

The copolymers of the invention can be prepared by copolymerizing acrylamide and sodium 2-acrylamido-2-methylpropanesulfonate via the free-radical route using azobiisobutyronitrile-type [sic] initiating agents and by precipitation in an alcohol such as tert-butanol.

The preferential copolymers are obtained by copolymerization of 70 to 55 mol % of acrylamide and of 30 to 45 mol % of sodium 2-acrylamido-2-methylpropanesulfonate, the crosslinking agent being used at concentrations of $10^{-4}$ to $4.10^{-4}$ mol per mole of the mixture of the monomers.

The copolymers are present in the aqueous dispersions of the invention at concentrations of between 0.05 and 10% by weight and preferably between 0.1 and 6% by weight.

A particularly preferred form of aqueous dispersion used in cosmetics or in topical application in accordance with the invention consists in using an aqueous dispersion containing:

a) an organopolysiloxane;

b) the crosslinked acrylamide/neutralized 2-acrylamido-2-methylpropanesulfonic acid copolymer;

c) a nonionic emulsifying agent;

d) one or a number of isoparaffin hydrocarbons having a high boiling point.

The isoparaffin hydrocarbon(s) is(are) present in proportions preferably of between 0.02 and 6.5% by weight with respect to the total weight of the dispersions.

In particular, there is used a mixture of $C_{12}$–$C_{13}$ isoparaffin hydrocarbons such as the product sold under the name Isopar M by the Company Exxon Chemicals.

Nonionic emulsifying agents used according to the invention are chosen, for example, from sorbitan fatty acid esters, fatty acid esters, ethoxylated fatty acid esters, fatty alcohols and ethoxylated fatty alcohols, block copolymers of ethylene oxide/propylene oxide or ethylene oxide/butylene oxide type, or their mixtures.

The emulsifying agents are preferably present in proportions of between 0.01 and 1.5% by weight with respect to the total weight of the dispersions. The ether of lauryl alcohol and of polyethylene glycol containing 7 mol of ethylene oxide is preferably used.

A particularly preferred form of aqueous dispersion used according to the invention contains an oil-in-water emulsion consisting of 35 to 45% by weight of crosslinked acrylamide/neutralized 2-acrylamido-2-methylpropane sulfonic acid copolymer, 15 to 25% of isoparaffin hydrocarbons, 3 to 8% by weight of the ether of lauryl alcohol and of polyethylene glycol containing 7 mol of ethylene oxide, and water. Such an emulsion is marketed under the name Sepigel 305 by the Company Seppic.

This particular aqueous dispersion, used according to the invention, is preferably prepared by simple mixing at room temperature and with stirring of the organosiloxane polymer with the emulsion as defined above. The mixture thus obtained can be introduced directly into the water containing other ingredients chosen according to the desired application.

The oil-in-water emulsion containing the particular copolymer of the invention as defined above is present in the aqueous dispersion in proportions such that the copolymer concentration is between 0.05 and 10% by weight and preferably 0.1 and 6% by weight of active copolymer material with respect to the total weight of the dispersion.

Another subject of the invention consists of a composition in the form of an aqueous dispersion intended for hair or skin treatment in cosmetics and/or in dermatology, characterized in that the aqueous dispersion is as defined above.

The compositions in accordance with the present invention can additionally contain adjuvants commonly used in cosmetics such as fragrances, dyes, preserving agents, sequestering agents, vegetable, animal or synthetic oils, sunscreening agents, anionic, nonionic, amphoteric or cationic surface-active agents, polymers, proteins, conditioning agents, foam stabilizing agents, propellants or other adjuvants commonly used in compositions for the hair or the skin, depending on the application envisaged.

The cosmetic compositions intended for hair treatment, in accordance with the invention, can be used in particular as a shampoo, as a rinsing product, to be applied before or after a shampoo, before, during or after dyeing or bleaching, before or after a permanent wave or hair straightening or in an intrapermanent lotion or as a non-rinsed styling product, as in hair setting or blow-drying lotions.

The cosmetic compositions in accordance with the present invention intended for skin treatment and care can be in the form of a product for the bath or the shower, of a tanning product, of a shaving product, of a scented lotion, of a cream or of a milk for skin care or anti-sun compositions.

Preferentially, when the compositions according to the invention contain detergent surface-active agents, the latter are present in a proportion of less than 5% by weight with respect to the total weight of the composition.

The compositions in accordance with the present invention can be applied in dermatology. They contain, in an effective quantity, a substance which is active on the dermatological level, such as, for example, vitamin A, carotenoids, proteins, natural pigments, retinoids, depigmenting agents, antiseborrheic substances, anti-acne substances, anti-inflammatory substances or anti-dandruff substances.

The cosmetic or dermatological compositions according to the present invention have a pH of between 3 and 10 and preferably between 5 and 7. This pH can be adjusted with basifying or acidifying agents commonly used in cosmetics and in dermatology.

A process for the cosmetic treatment of hair according to the invention consists in applying the compositions as defined above to the hair depending on the envisaged use (shampoo, rinsing treatment, styling treatment without rinsing), without it being necessary to observe a development time, and optionally in rinsing.

A process for the cosmetic treatment of the skin according to the invention consists in applying to the latter a composition as defined above, depending on the envisaged use (bath, shower, tanning products, shaving products, scented lotions, care creams or milks), and optionally in rinsing.

The examples which follow are intended to illustrate the present invention without having in any way a limiting nature.

EXAMPLE 1

A non-rinsed care composition is prepared:

| | |
|---|---|
| oil-in-water emulsion of crosslinked acrylamide/sodium 2-acrylamido-2-methylpropane-sulfonate copolymer, sold by the Company Seppic under the name Sepigel 305 | 0.17 g as copolymer |
| Mixture of dimethiconol (13%), octamethylcyclotetrasiloxane and decamethylcyclopentasiloxane (87%), sold under the name Q2-1401 by the Company Dow Corning | 15 g |
| Polydiorganosiloxane having a thiol functional group of formula: | 5 g |

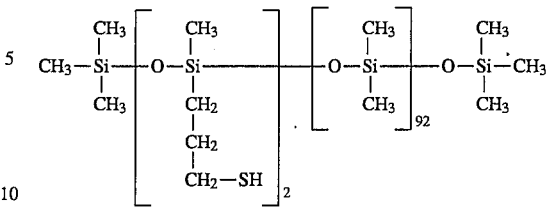

| | |
|---|---|
| sold under the name X2 8360 by the Company Dow Corning | |
| Preserving agent, fragrance | qs |
| Spontaneous pH = 6.3 | |
| Water | qs for 100 g |

EXAMPLE 2

A non-rinsed care composition is prepared:

| | |
|---|---|
| Oil-in-water emulsion of crosslinked acrylamide/sodium 2-acrylamido-2-methylpropanesulfonate copolymer sold by the Company Seppic under the name Sepigel 305 | 0.14 g as copolymer |
| Polydimethylmethyltrifluoro-propylsiloxane, sold by the Company Shin Etsu under the name X-22-821 | 20 g |
| Preserving agent, fragrance | qs |
| Spontaneous pH = 7.2 | |
| Water | qs for 100 g |

EXAMPLE 3

A non-rinsed care composition is prepared:

| | |
|---|---|
| Oil-in-water emulsion of crosslinked acrylamide/sodium 2-acrylamido-2-methylpropane-sulfonate copolymer, sold by the Company Seppic under the name Sepigel 305 | 0.35 g as copolymer |
| Polydimethylsiloxane (MW 250,000), sold under the name 47 V 500.000 by the Company Dow Corning | 5 g |
| Preserving agent, fragrance | qs |
| HCl qs pH = 5 | |
| Water | qs for 100 g |

EXAMPLE 4

A rinsing after-shampoo of the following composition is prepared:

| | |
|---|---|
| Oil-in-water emulsion of crosslinked acrylamide/sodium 2-acrylamido-2-methylpropanesulfonate copolymer, sold by the Company Seppic under the name Sepigel 305 | 0.21 g as copolymer |
| Polydiorganosiloxane of formula: 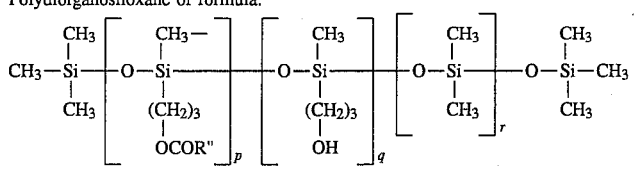 | |

R" = mixture of $C_{16}H_{33}$ and $C_{18}H_{37}$ radicals
p = 7.9, q = 1.4, r = 9.3

This compound contains on average 2

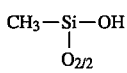

units.

It can be prepared as described in Example A of Application FR-2,64 1,185.

| | |
|---|---|
| Preserving agent, fragrance | qs |
| Spontaneous pH = 7.5 | |
| Water | qs for 100 g |

EXAMPLE 5

A rinsing after-shampoo of the following composition is prepared:

| | |
|---|---|
| Oil-in-water emulsion of crosslinked acrylamide/sodium 2-acrylamido-2-methylpropane-sulfonate copolymer, sold by the Company Seppic under the name Sepigel 305 | 0.14 g as copolymer |
| Mixture of dimethiconol (13%), octamethylcyclotetrasiloxane and decamethylcyclopentasiloxane (87%), sold under the name Q2-1401 by the Company Dow Corning | 20 g |
| Preserving agent, fragrance | qs |
| Spontaneous pH = 7.6 | |
| Water | qs for 100 g |

EXAMPLE 6

An after-shampoo of the following composition is prepared:

| | |
|---|---|
| Oil-in-water emulsion of acrylamide/sodium acrylamido-2-methylpropanesulfonate [sic] copolymer, sold by the Company Seppic under the name Sepigel 305 | 1.5 g as copolymer |
| Nonionic microemulsion containing 30% of aminated silicone oil (amodimethicone with a viscosity $3.10^{-4}$ m²/s), sold by the Company Rhône-Poulenc | 3 g as silicone |
| Preserving agent, fragrance | qs |
| Spontaneous pH = 6.5 | |
| Water | qs for 100 g |

EXAMPLE 7

An anti-sun emulsion of the following composition is prepared:

| | |
|---|---|
| Oil-in-water emulsion of acrylamide/sodium acrylamido-2-methylpropanesulfonate [sic] copolymer, sold by the Company Seppic under the name Sepigel 305 | 3.2 g as copolymer |
| Mixture of dimethiconol (13%), octamethylcyclotetrasiloxane and decamethylcyclopentasiloxane (87%), sold by the Company Dow Corning under the name Q2-1401 | 7.5 g |
| Liquid paraffin | 5 g |
| Mixture of glycerol stearate and of polyethylene glycol stearate containing 100 mol of ethylene oxide, sold by the Company ICI under the name Arlacel 165 | 3 g |
| 2-Ethylhexyl p-methoxycinnamate sold by the Company Givaudan under the name Parsol MCX | 6 g |
| Preserving agent, fragrance | qs |
| Water | qs for 100 g |

EXAMPLE 8

An after-sun product of the following composition is prepared:

| | |
|---|---|
| Oil-in-water emulsion of acrylamide/sodium acrylamido-2-methylpropanesulfonate [sic] copolymer, sold by the Company Seppic under the name Sepigel 305 | 1.2 g as copolymer |
| Mixture of dimethiconol (13%), octamethylcyclotetrasiloxane and decamethylcyclopentasiloxane (87%), sold by the Company Dow Corning under the name Q2-1401 | 15 g |
| α-Bisabolol (terpene derivative) sold by the Company Dragoco under the name Dragosantol | 0.3 g |

-continued

| | |
|---|---|
| Glycerol | 5 g |
| Mixture of glycerol stearate and of polyethylene glycol stearate containing 100 mol of ethylene oxide, sold by the Company ICI under the name Arlacel 165 | 5 g |
| Preserving agent, fragrance | qs |
| Water | qs for 100 g |

EXAMPLE 9

An after-shampoo of the following composition is prepared:

| | |
|---|---|
| Oil-in-water emulsion of acrylamide/sodium acrylamido-2-methylpropanesulfonate [sic] copolymer, sold by the Company Seppic under the name Sepigel 305 | 2 g as copolymer |
| Mixture of dimethiconol (13%), octamethylcyclotetrasiloxane and decamethylcyclopentasiloxane (87%), sold by the Company Dow Corning under the name Q2-1401 | 5 g |
| Polymer of hydroxyethyl cellulose and of epichlorohydrin quaternized with trimethylamine, sold by the Company Union Carbide under the name JR 400 | 1 g |
| Preserving agent, fragrance | qs |
| Triethanolamine qs pH = 6.5 | |
| Water | qs for 100 g |

EXAMPLE 10

A rinsing after-shampoo composition is prepared:

| | |
|---|---|
| Oil-in-water emulsion of acrylamide/sodium acrylamido-2-methylpropanesulfonate [sic] copolymer, sold by the Company Seppic under the name Sepigel 305 | 10 g as copolymer |
| Mixture of two polydimethylsiloxanes having different viscosities, sold by the Company General Electric under the name CF 1241 | 4.5 g |
| Preserving agent | qs |
| Spontaneous pH = 5.5 | |
| Water | qs for 100 g |

EXAMPLE 11

A rinsing after-shampoo composition is prepared:

| | |
|---|---|
| Oil-in-water emulsion of acrylamide/sodium acrylamido-2-methylpropanesulfonate [sic] copolymer, sold by the Company Seppic under the name Sepigel 305 | 5 g as copolymer |
| Polydimethylsiloxane (MW 250,000) sold by the Company Dow Corning under the name 70047 V 500.000 | 3 g |
| Preserving agent | qs |
| Triethanolamine qs pH = 7.2 | |
| Water | qs for 100 g |

We claim:

1. An aqueous dispersion for use in cosmetics or in topical application comprising, in a cosmetically or physiologically acceptable aqueous medium, at least one organopolysiloxane and one crosslinked acrylamide neutralized 2-acrylamido-2-methylpropanesulfonic acid copolymer, the organopolysiloxane is selected from the group consisting of (i) cyclic silicons containing 3 to 7 silicon atoms or cyclocopolymers of dimethylsiloxane/methylalkylsiloxane type;

(ii) linear silicons having 2 to 9 silicon atoms and having a viscosity less than or equal to $5.10^{1-6}$ m$^2$/s at 25° C.;

(iii) polyalkylsiloxane;

(iv) polyarylsiloxane;

(v) polyalkylarylsiloxane;

(vi) silicon gums;

(vii) silicon resins;

(viii) organomodified polysiloxanes and their mixtures, the organopolysiloxane is present in proportions of between 0.5 and 50% by weight with respect to the total weight of the dispersion and the copolymer is present in proportions of between 0.05 and 10% by weight with respect to the total weight of the dispersion, with the proviso that the organopolysiloxane is not chosen from linear polydimethylsiloxanes with a viscosity of less than $10^{-1}$ m$^2$/s, the copolymer is obtained by copolymerization of 70 to 55 mol % of acrylamide and 30 to 45 mol % of sodium 2-acrylamido 2-methylpropanesulfonate in the presence of $10^{-4}$ to $4.10^{-4}$ mol of crosslinking agents per mol of mixture of the two monomers.

2. The aqueous dispersion according to claim 1, wherein the organopolysiloxane is selected from the group consisting of:

A) poly($C_1$–$C_{20}$)alkylsiloxanes, linear polydimethylsiloxanes containing trimethylsilyl end groups and linear polydimethylsiloxanes containing trihydroxysilyl end groups, with a viscosity greater than $10^{-1}$ m$^2$/s;

B) linear and/or branched polydimethyldiphenylsiloxanes and polydimethylphenylsiloxanes, with a viscosity $10^{-5}$ to $5.10^{-2}$ m$^2$/s at 25° C.;

C) gums with a molecular mass of between 200,000 and 1,000,000, used alone or in the form of a mixture in a solvent, selected from the group consisting of the following copolymers:
poly[dimethylsiloxane/methylvinylsiloxane],
poly[dimethylsiloxane/diphenylsiloxane],
poly[dimethylsiloxane/phenylmethylsiloxane], and
poly[dimethylsiloxane/diphenylsiloxane/methylvinylsiloxane]
and the following mixtures:
mixtures formed from a polydimethylsiloxane hydroxylated at the chain ends and from a cyclic polydimethylsiloxane,
mixtures formed from a polydimethylsiloxane gum and from a cyclic silicone, and
mixtures of two polydimethylsiloxanes having different viscosities;

D) organopolysiloxane resins containing $R_2SiO_{2/2}$, $RSiO_{3/2}$ and $SiO_{4/2}$ units in which R represents a hydrocarbon group having 1 to 6 carbon atoms or a phenyl group.

3. The aqueous dispersion according to claim 1 wherein the organopolysiloxane contains in its general structure one or a number of organofunctional group(s) attached directly to the siloxane chain or attached via a hydrocarbon radical, and in that it is selected from the group consisting of polyorganosiloxanes containing:

a) polyoxyethylene and/or polyoxypropylene groups,
b) perfluorinated groups,
c) hydroxyacylamino groups,
d) thiol groups,
e) substituted and unsubstituted amino groups,
f) carboxylate groups,
g) hydroxyalkyl groups of formula:

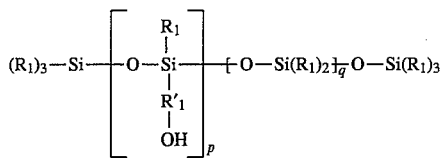

in which
the radicals $R_1$, which are identical or different, are selected from the group consisting of methyl and phenyl radicals, at least 60 mol% of the radicals $R_1$ being methyl,
the radical $R'_1$ is a divalent $C_2$–$C_{18}$ alkylene hydrocarbon chain,
p is between 1 and 30 inclusive;
q is between 1 and 150 inclusive;

h) alkoxylated groups,
i) acyloxyalkyl groups corresponding to the following formula:

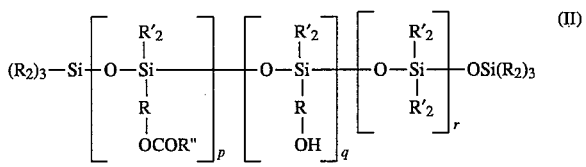

in which:
$R_2$ denotes methyl, phenyl, OCOR" or hydroxyl, a single one of the $R_2$ groups per silicon atom being OH,
$R'_2$ denotes methyl or phenyl, at least 60 mol % of the combined radicals $R_2$ and $R'_2$ are methyl,
R" denotes $C_8$–$C_{20}$ alkyl or alkenyl,
R denotes a linear or branched, divalent $C_2$–$C_{18}$ alkylene hydrocarbon,
r is between 1 and 120, inclusive,
p is between 1 and 30,
q has the value 0 or is less than 0.5 p, p+q being between 1 and 30,
the polyorganosiloxanes of formula (II) containing

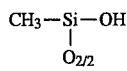

groups in proportions not exceeding 15% of the sum p+q+r, j) quaternary ammonium groups,
k) amphoteric or betaine groups, and
l) bisulfite groups.

4. The aqueous dispersion according to claim 1, wherein the organopolysiloxane is selected from the group consisting of:

1) nonvolatile silicones of linear polyalkylsiloxane type containing trimethylsilyl end groups or of polyalkylphenylsiloxane type, 2) mixtures of organosiloxanes and of cyclic silicones, 3) fluorosilicones of polyalkylsiloxane type containing trimethylsilyl end groups and substituted on the chain by trifluoropropyl groups.

5. The aqueous dispersion according to claim 1 wherein the acrylamide/2-acrylamido-2-methylpropanesulfonic acid copolymer is crosslinked with a crosslinking agent containing olefinic polyunsaturation selected from the group consisting of tetraallyloxyethane, allylsucrose, allylpentaerythritol and methylenebisacrylamide and in that it is partially or completely neutralized by sodium hydroxide, potassium hydroxide, aqueous ammonia or an amine.

6. The aqueous dispersion according to claim 1 wherein the aqueous dispersion comprises:
a) the organopolysiloxane,
b) the crosslinked acrylamide/neutralized 2-acrylamido-2-methylpropanesulfonic acid copolymer,
c) a nonionic emulsifying agent,
d) an isoparaffin hydrocarbon or a mixture of isoparaffin hydrocarbons having a high boiling point.

7. The aqueous dispersion according to claim 6, wherein the emulsifying agent is selected from the group consisting of sorbitan fatty acid esters, ethoxylated and non-ethoxylated fatty acid esters, ethoxylated and non-ethoxylated fatty alcohols, and block copolymers of ethylene oxide/propylene oxide and ethylene oxide/butylene oxide type, and their mixtures.

8. The aqueous dispersion according to claim 6, wherein the emulsifying agent is present in proportions of between 0.01 and 1.5% by weight and in that the isoparaffin hydrocarbon(s) are present in proportions of between 0.02 and 6.5% by weight with respect to the total weight of the dispersion.

9. The aqueous dispersion according to claim 6 wherein the nonionic emulsifying agent is the ether of lauryl alcohol and of polyethylene glycol containing 7 mol of ethylene oxide and in that a mixture of $C_{12}$–$C_{13}$ isoparaffin hydrocarbons is used.

10. The aqueous dispersion according to claim 1, wherein the crosslinked acrylamide/neutralized 2-acrylamido-2-methylpropanesulfonic acid copolymer is dispersed at a concentration of 35 to 45% by weight in an oil-in-water emulsion containing 15 to 25% by weight of a mixture of $C_{12}$–$C_{13}$ isoparaffin hydrocarbons, 3 to 8% by weight of ether of lauryl alcohol and of polyethylene glycol containing 7 mol of ethylene oxide, and water.

11. The aqueous dispersion according to claim 10, wherein the oil-in-water emulsion containing the crosslinked acrylamide/neutralized 2-acrylamido-2-methylpropanesulfonic acid copolymer is present in the aqueous dispersion in proportions such that the copolymer concentration is between 0.05 and 10% by weight of active material with respect to the total weight of the dispersion.

12. Cosmetic composition in the form of an aqueous dispersion intended for hair or skin treatment, wherein the aqueous dispersion is as defined in claim 1.

13. Composition according to claim 12, further comprising adjuvants commonly used in cosmetics, chosen from fragrances, dyes, preserving agents, vegetable, animal or synthetic oils, proteins, conditioning agents, anionic, nonionic, amphoteric or cationic surface-active agents, sequestering agents, foam stabilizing agents, polymers, sunscreening agents, propellants or substances active on the cosmetic level.

14. Composition according to either of claims 12 or 13, wherein it has a pH of between 3 and 10.

15. Composition according to claim 12 intended for hair treatment, wherein it is provided in the form of a shampoo, of a rinsing product, to be applied before or after a shampoo, before, during or after dyeing or bleaching, before or after a permanent wave or hair straightening, in an intrapermanent lotion or as non-rinsed styling products.

16. Composition according to claim 12, intended for skin treatment, wherein it is provided as a bath or shower product, tanning product, anti-sun composition, shaving product, care cream or milk or scented lotion.

17. Process for cosmetic hair treatment, wherein at least one composition as defined in claim 15 is applied to the hair.

18. Process for cosmetic skin treatment, wherein a composition as defined in claim 16 is applied to the skin.

19. Dermatological composition in the form of an aqueous dispersion, wherein the aqueous dispersion is as defined in claim 1 and in that it contains, in an effective quantity, at least one substance which is active on the dermatological level.

20. The aqueous dispersion of claim 1 wherein the cyclic silicones contain 4 to 5 silicon atoms.

21. Composition according to claim 12, wherein it has a pH of between 5 and 7.

* * * * *